United States Patent [19]

Aivasidis et al.

[11] Patent Number: 4,532,042

[45] Date of Patent: Jul. 30, 1985

[54] PROCESS AND APPARATUS FOR THE CONTINUOUS ANAEROBIC DECOMPOSITION OF ORGANIC COMPOUNDS

[75] Inventors: Alexander Aivasidis; Christian Wandrey, both of Jülich, Fed. Rep. of Germany

[73] Assignee: Kernforschungsanlage Jülich Gesellschaft mit beschränkter Haftung, Jülich, Fed. Rep. of Germany

[21] Appl. No.: 562,841

[22] Filed: Dec. 19, 1983

[30] Foreign Application Priority Data

Dec. 20, 1982 [DE] Fed. Rep. of Germany ....... 3247117

[51] Int. Cl.³ .............................................. C02F 3/28
[52] U.S. Cl. .................................... 210/603; 201/614; 201/617; 201/96.1; 201/150; 201/196
[58] Field of Search ............... 210/603, 614, 617, 618, 210/150, 151, 96.1, 218, 194, 196, 743; 435/167, 801, 291

[56] References Cited

U.S. PATENT DOCUMENTS

| 4,284,508 | 8/1981 | Jewell | 210/603 |
| 4,349,435 | 9/1982 | Ochiai | 201/614 |
| 4,351,729 | 9/1982 | Witt | 210/603 |
| 4,352,738 | 10/1982 | Blay et al. | 210/614 |

FOREIGN PATENT DOCUMENTS

| 0028846 | 8/1980 | European Pat. Off. | |
| 0046901 | 8/1981 | European Pat. Off. | |
| 0057152 | 1/1982 | European Pat. Off. | |
| 58-11100 | 1/1983 | Japan | 210/603 |
| 2014555 | 2/1979 | United Kingdom | |
| 2082164 | 2/1982 | United Kingdom | 210/617 |

OTHER PUBLICATIONS

"Reinigung organisch hochverschmutzter Abwässer mit dem anaeroben Belebungsverfahren am Beispiel von Abwässern der Nahrungsmittelherstellung", Von der Fakultät für Bauwesen der Universität Hannover zur Erlangung des Grades, Doktor-Ingenieur, genehmigte Dissertation, Dipl-Ing. Helmut Sixt, 1979, pp. 254-259.

Primary Examiner—Benoit Castel
Attorney, Agent, or Firm—Nils H. Ljungman

[57] ABSTRACT

Process and apparatus for the continuous anaerobic decomposition of organic compounds in an aqueous liquid is effected, in accordance with the invention, in a fixed-bed reactor by microorganisms, which are grown upon a support with the admixture of recycled reactor discharge in such an amount that practically uniform conditions exist throughout the reactor. The volume/-time yield can be increased to a surprisingly large extent by means of the process if, after breeding sufficient adhering microorganisms with a residence time equal to or greater than 50% of the doubling time, an iterative reduction is efected in the residence time with the onset of equilibrium conditions at each stage until the volume/time yield can be increased no further.

16 Claims, 2 Drawing Figures

PROCESS AND APPARATUS FOR THE CONTINUOUS ANAEROBIC DECOMPOSITION OF ORGANIC COMPOUNDS

BACKGROUND OF THE INVENTION

The invention is related to waste treatment and, particularly, to a method and apparatus for the continuous anaerobic decomposition of organic compounds.

As interest in environmental safety grows, governmental agencies continuously issue more and more stringent standards concerning fluid waste disposed by, for example, industries into publicly owned treatment facilities. As a result, industries, which had heretofore only provided primary treatment to remove solid waste from fluid waste, are now faced with the necessity of providing secondary or biological treatment to remove soluble waste products from the fluid waste. Additionally, discharging industries are often faced with the burden of paying surcharges for discharging inadequately treated effluent into public works.

Biological waste treatment units have been very expensive to install and operate. Moreover, while numerous types of such treatment units are available, they share the common drawback of long waste treatment times and the resulting low volume/time yield of processed waste. In general, anaerobic microbial processes proceed very slowly and, moreover, due to the poor utilization of the carbon source resulting from the anaerobically growing cells (ATP-formation), the bacteria concentrations are low compared with those from an aerobic process. Consequently, continuous operation in, for example, a stirred vessel reactor, results in long residence times and low volume/time yields. By reducing the residence time to below the critical value, which corresponds to the reciprocal of the maximum growth-rate $MY_{max}$, the microorganisms are washed out of the system and the process tends to become unstable if the reactor waste feed is not strictly regulated.

It is, however, possible to increase the volume/time yield if, on reducing the hydraulic residence time, the biomass is either retained in the reactor or is separated outside of the reactor and returned to the reactor vessel.

To be sure, processes based on the sedimentation of microorganisms have low efficiency and are strongly dependent on the settling ability of the cells, which can be impaired by the formation of biogas and by flotation.

While filtration is possible in principle, it requires, of course, special filtering units and is too expensive for treating significant quantities of liquid. An example of such a biological filtration treatment technique can be found in U.S. Pat. No. 3,732,160 which discloses the use of a submerged filter-horizontal flow method for wastewater treatment with a bacterial culture build up on a filter medium. The medium is graded progressively finer in the direction of the flow of the wastewater which is continuously recirculated through the medium.

Another example is European Patent Application No. 0,028,846 which teaches that an effective method of retaining biomasses within a reactor vessel is allowing the microorganism to grow on an inert carrier. In this technique, the waste liquid to be treated is fed continuously into a reactor charged with a suspension of bacteria, the process being such that a residence time is maintained which is below the wash-out point. Under these conditions, a process of selection takes place in which only those microorganisms, which develop suitably strong adhesion forces with respect to the support and which can take nourishment from the proffered carbon source, can multiply. The selectivity can also be a function of the presence of shear force effects, the intensity of which is a function of the waste liquid's rate of flow.

The above-described reaction in a fluidized bed reactor is advantageous in that a high incident flow velocity can be chosen to effect microorganism growth, in that no problem results from the separation of the biogas and in that approximately uniform conditions are present in the reactor. However, allowance must be made for the relatively high amount of abrasion product due to intense fluid bed motion and for the loss of bacteria as a result thereof. Moreover, a relatively large amount of energy is required to reach the fluidizing point.

On the other hand, the continuous flow-through fixed-bed reactor, as taught by the aforedescribed U.S. Patent, has the advantage of low abrasion loss and low energy consumption. However, only relatively low flow rates are possible and pockets of biogas form dead spaces in the reactor. There are the additional disadvantages of a blockage due to suspended solids, and also, a concentration and pH gradient within the reactor from the inlet end to the outlet ends thereof.

Several factors which are of importance in the decomposition of acetic acid in a waste solution have not been satisfactorily addressed by the techniques heretofore available in waste treatment. These factors include: the high chemical oxygen consumption of the acetic acid-containing waste product to be treated; its low pH, typically in the range of between about 2 to 4; the long doubling time of the microorganisms utilized in the process; a limited tendency to form large aggregates or flocculations; and the fact that the optimum pH for microorganism growth lies in a pH range of between about 6 to 7.2. The aforedescribed factors thus result in the necessity of establishing a long residence time for the waste liquid to be treated by the reactor bed material. Accordingly, the achievable volume/time yields are small. Additionally, it is necessary to monitor the pH of the waste liquid to be treated and typically bring it to the optimum value by the addition of a buffer or alkali before the liquid waste enters the reactor vessel. These limitations in the available waste treatment techniques render a process which can best be characterized as having unsatisfactory efficiency in secondary waste treatment.

It is, therefore, an object of this invention to improve the efficiency of an anaerobic decomposition process, particularly, an acetic acid-methanization process in a fixed-bed reactor.

It is also an object of this invention to provide a reactor apparatus for effecting the process of this invention.

It is yet another object of this invention to provide a process for the continuous anaerobical decomposition of organic compounds in an aqueous solution which does not require the addition of chemicals to maintain the pH of the reactor bed within the optimum range for the growth of bacteria.

It is still another object of this invention to provide a process and an apparatus by which a rapid rate of flow of liquid waste through a reactor bed can be established and maintained and whereby practically uniform pH conditions exist throughout the reactor bed.

It is a further object of this invention to provide a process and apparatus whereby anaerobic decomposition takes place throughout the entire reactor bed while substantially eliminating gas blockages within the reactor through satisfactory gas release above the reactor bed.

SUMMARY OF THE INVENTION

The invention is a fixed-bed column reactor and a process for the continuous anaerobic decomposition of organic compounds in an aqueous solution within the reactor. The reactor vessel includes a bottom feed, an upper discharge and means for recycling a portion of the discharged aqueous solution to the bottom feed. A pH sensor is disposed at both the lower and upper ends of the reactor in order to provide pH measurements of the solution within the reactor bed. Means, responsive to the pH measurements, select the portion of the discharged aqueous solution to be recycled through the reactor with additional waste feed. The recycled portion is selected to maintain the pH level within the reactor bed within a predetermined range.

BRIEF DESCRIPTION OF THE DRAWINGS

The above, as well as other features and advantages of this invention, will become apparent through consideration of the detailed description in connection with the accompanying drawings in which.

DETAILED DESCRIPTION OF THE INVENTION

Figure 1:
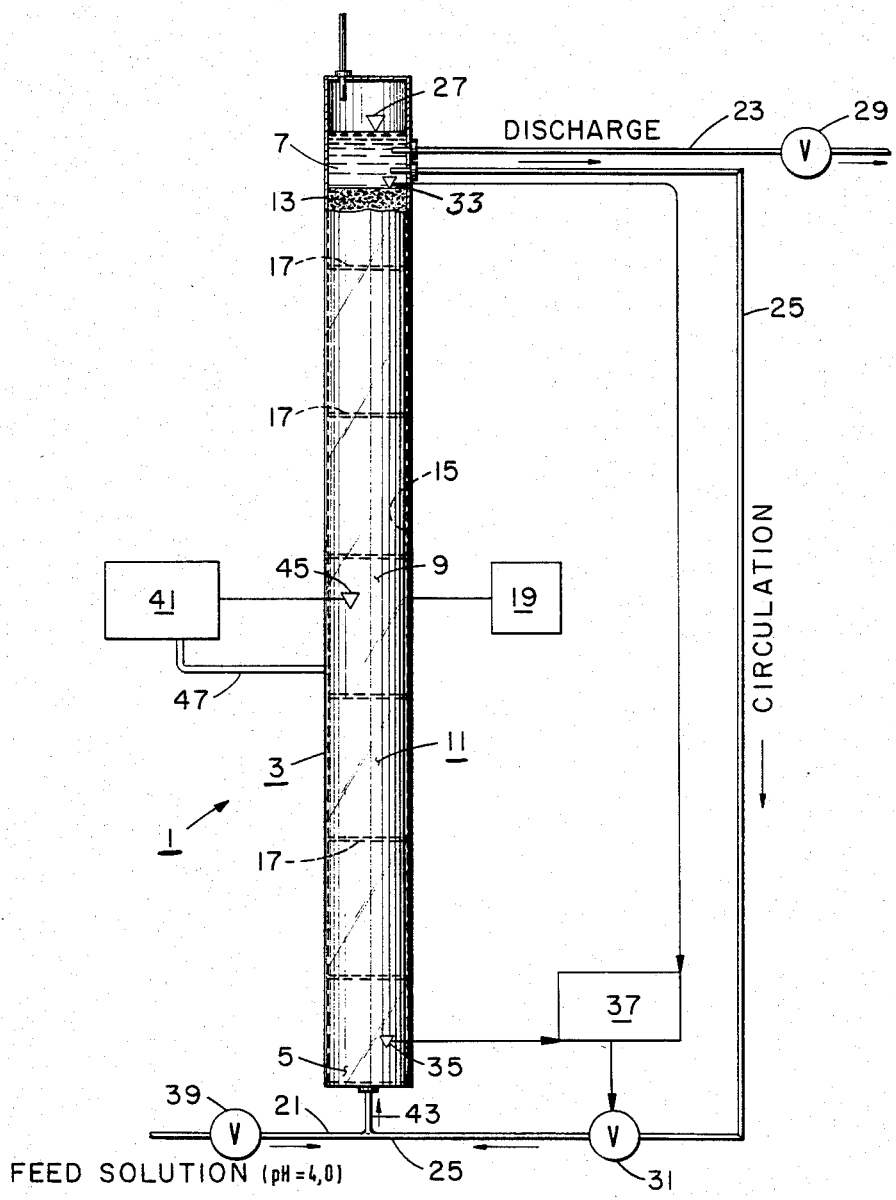
FIG. 1 is a side elevation, schematical representation of a vertical fixed-bed reactor incorporating the features of this invention.

The invention provides both a process and an apparatus for the continuous anaerobical decomposition of organic compounds in an aqueous feed solution. An apparatus by which the process of the invention is effectively carried out is schematically represented in FIG. 1 and generally indicated by the reference character 1. The apparatus 1, a vertical fixed-bed reactor, includes a reactor vessel 3 having a bottom end 5, an upper end 7 and a central region 9. A fixed reactor bed 11 is defined within the reactor vessel 3 by reactor bed material 13 (only a portion of which is illustrated) which is described in detail below. The reactor vessel 3 has a filling height to diameter ratio of between about 8:1 and 6:1, preferably, 12:1. The interior wall 15 of the reactor vessel 3 is provided with a plurality of regularly spaced, ring shaped inserts as at 17 which function as baffles to inhibit the formation of channels along the walls of the fixed-bed reactor material 13. The temperature of the reactor vessel 3 is maintained between about 30° to 40° C. through the use of conventional thermostat and temperature control means schematically indicated at 19. Preferably, the temperature is maintained at about 37° or 38° C.

At the first end or bottom 5 of the reactor vessel 3, means as at 21 are provided to introduce an aqueous feed solution into the lower portion of the reactor bed 11. At the second end or upper portion 7 of the reactor vessel 3, means are provided to receive and discharge the treated aqueous solution from the reactor bed 11. The discharging and receiving means, as illustrated, comprise a first conduit 23 and a second conduit 25, respectively. The second conduit 25 is in communication with the solution introduction means or conduit 21 at the bottom of the reactor vessel 3.

Located near the top of the reactor vessel 3 is a conventional fluid level sensor 27 for setting a maximum limit on the filling height of the reactor. The level sensor 27 is in communication with and in control over a valve or pump means 29 by which the treated liquid is drawn from the top of the reactor vessel 3 via conduit 23 for further disposition external to the process and apparatus of the invention. By employing different filling heights, it is possible to change the free contact volume on which can be based the requisite residence time. The second conduit 25 is in communication with conduit 21 via control valve or pump means 31 which introduces a determinable portion of the treated liquid from the top of the reactor back into the lower portion thereof for recirculation of the liquid therethrough.

Means for monitoring the pH of the liquid within the reactor bed 11 are disposed at the upper and lower portions of the reactor vessel 3 as at 33 and 35 respectively. The monitoring means 33 and 35 are in communication with a control means 37 which in turn effects the aforedescribed pump means 31 of the second conduit 25. The pH of the liquid at the upper and lower ends of the reactor vessel 3 is monitored according to a predetermined schedule in order to adjust the ratio of recirculated treated liquid from the conduit 25 to the solution of untreated liquid from the conduit 21 to be introduced into the lower portion of the reactor vessel 3 through the conduit 43. This ratio adjustment is effected in order to maintain an approximately uniform pH throughout the reactor vessel 3. It has been found that the circulation of treated liquid typically amounts to about 15 to 20 times the volume of untreated liquid. Valve means as at 39 can be associated with waste feed line 21 in order to control the volume of untreated liquid introduced into the reactor vessel 3.

The reactor vessel 3 also includes an emergency system schematically represented in block diagrammatic form at 41, and located in the central region 9 of the reactor vessel 3. The emergency system 41 monitors the pH of the liquid within the reactor vessel 3 with a pH monitor 45 so that in the event that the equalizing of the pH cannot be achieved by controlling the circulation of treated liquid back into the lower region of the reaction zone, a correcting agent can be introduced into the reactor vessel 3 through conduit 47. Thus, if a pH beyond a predetermined range is monitored, the emergency system 41 provides sufficient correcting agent to return the fluid within the reactor vessel 3 to the desired pH range.

The fixed-bed material 13 within the reactor vessel 3 is a material suitable for supporting the desired microorganisms and has a grain size of between about 2 to 8 mm, preferably 4 to 6 mm. It has been determined that anthracite coal is an especially advantageous support material. Anthracite coal is a very hard support material which undergoes low abrasion loss and possesses an irregular surface which enhances microorganism growth. For purposes of the experimental application of this invention, as described hereinafter, Filter Anthracite N ® supplied by PREUSSAG AG from the Ibbenbüren seam served as the support material. This anthracite has the following characteristic properties:

| | |
|---|---|
| Density | 1.40–1.45 g/cm$^3$ |

| | -continued | | |
|---|---|---|---|
| Bulk density | 740 kg/m$^3$ | | |
| Carbon content | greater than 90% | | |
| Grain size | Type 1 | Type 2 | Type 3 |
| | 0.8–1.6 mm | 1.4–2.5 mm | 2.5–4.0 mm |

The anthracite is a natural product which is mined, crushed and sieved. It is a non-porous material with a well-defined granularity.

The continuous anaerobic decomposition of organic compounds, in accordance with this invention, is characterized in that the liquid is fed into a fixed-bed reactor vessel 3 having microorganisms grown on a solid support, and the liquid is mixed with a portion of recycled reactor discharge which holds the pH of the reactor liquid, measured at the lower and upper ends of the fixed reactor bed 11, in a narrow range which does not exceed approximately 0.3 pH units within a pH range of between about 6 to 7.2. This process provides a rapid rate of flow through the reactor vessel 3 so that practically uniform conditions exist in the reactor and the decomposition takes place throughout the entire fixed reactor bed 11 within the reactor vessel 3. Moreover, recycling, according to this invention, maintains the pH of the reactor liquid within the optimum range for the growth of bacteria and, as a result, the conventional requirement of selective chemical admixture within the reactor vessel to ensure suitable bacterial growth conditions within the reactor is substantially eliminated.

The efficiency of such a fixed-bed reactor operation, with microorganisms bred by autoselection on a support, is considerably improved, according to this invention. In the starting phase, the breeding of adequate adhering microorganisms occurs only with a mean direct contact time which is not less than 50% of the participating microorganisms' doubling time. Depending on whether such breeding has been successful, the reactor's volume/time yield can be increased by reducing the mean residence time. The reduction is effected by proceeding in relatively small steps, allowing equilibrium to set in at each step. It should be noted that a reduction in the residence time of 50% or more, typically renders a completely negative result, that is, the microorganisms are washed completely out of the reactor so that, all in all, an increase in the output is most unlikely.

In the preferred embodiment of the invention, after the first breeding with a residence time which is not less than 50% of the doubling time of the participating organisms, a repeated reduction of the residence time is consequently undertaken until no further increase can be obtained in the volume/time yield of the treatment process.

The process of this invention was tested in a scaled apparatus of the design schematically represented in FIG. 1 and essentially constructed from a plexiglass column with a height of 65 cm and a diameter of 5 cm, and with a filling height to diameter ratios of 12:1. The temperature of the reactor vessel 3 was held to about 37°–38° C. by thermostatic control. The microorganism affixed on the granular support material was methanosarcina barkeri. To test the continuous decomposition process of this invention, use was made of acetic acid-containing test water which was provided with vitamins as well as with minerals and trace elements. The water had a chemical oxygen demand of about 20 kg/m$^3$ and a pH of 4. In this test, the supply or feed stream and the recycled stream were separately measured, to establish the correct ratio therebetween, and combined prior to entry into the reactor's lower region 5 (as at 43 in FIG. 1).

To start up the reactor apparatus 1 prior to actual continuous operation, the feed supply was set at a flow rate of 10 ml/hour with a residence time of 3.1 days. The feed pH was neutralized to 5.0 in order to prevent over-acidification in the fixed reactor bed 11 due to initially low decomposition rates.

After about two weeks, a sufficiently large bacteria population had formed on the support (recognizable by the acetic acid decomposition rate and the formation of biogas in the reactor), so that the supply could be fed at a faster rate, stepwise, through the reactor without previously adjusting the pH, as a result of which the residence time was correspondingly reduced.

Figure 2:
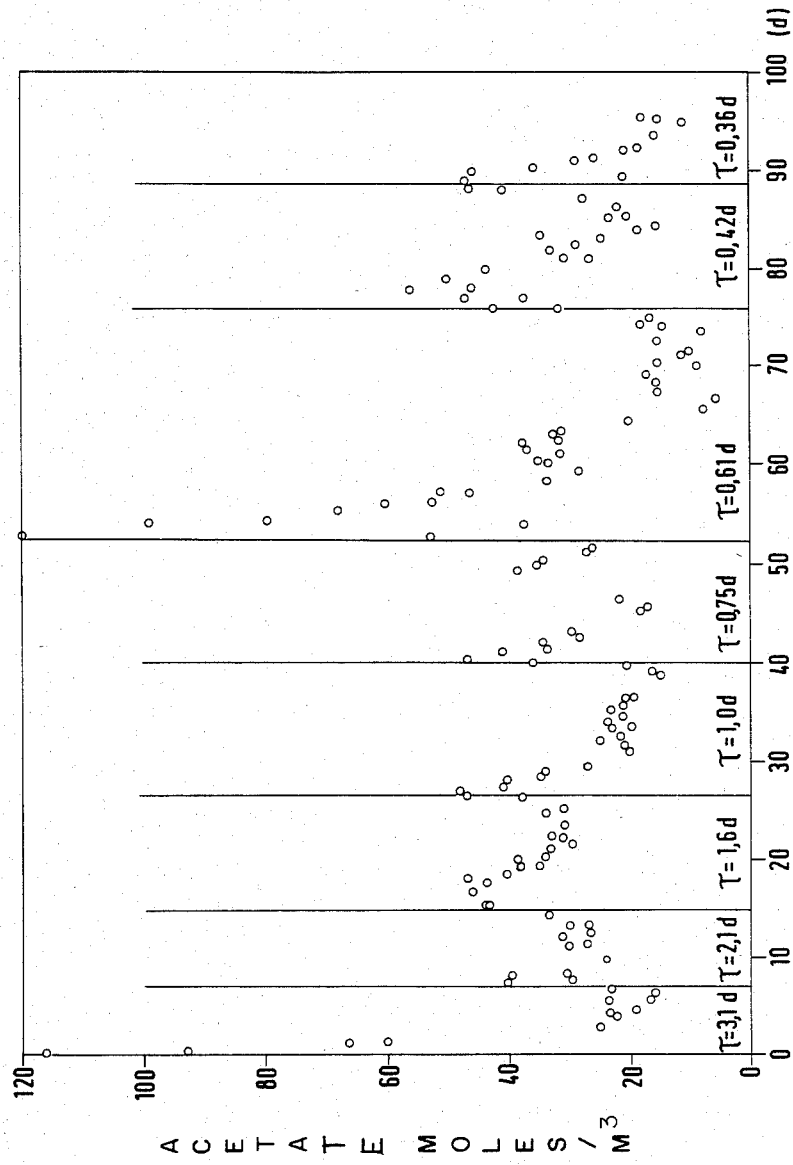
FIG. 2 is a graph representing a series of measurements which demonstrate the dynamic behavior of a fixed-bed reactor incorporating the shortened residence time of the waste fluid and the reactor bed, all according to the teachings of this invention.

FIG. 2 shows the acetate concentration in the reactor discharge as a function of the time for different residence times. As may be seen, the residence time was reduced by about 30% from step to step and the changed conditions were retained about 12 days.

As may be seen, the concentration of acetic acid increases after each reduction in the residence time because, initially, the bacteria population grown under the stationary conditions of the preceding stage is unable to treat the excessive supply of organic sources of carbon. (Especially large increases result in an initial "washout" of microorganisms caused by the increase in flow-through.)

However, as shown in the graph of FIG. 2, more biomass is formed as the process continues and the acetic acid is largely decomposed once again. After equilibrium has been established, this procedure of reducing the residence time with the onset of equilibrium is repeated until a distinct worsening in the acetic acid transformation is observed or a further increase in the volume/time yield is no longer possible. In the present test, it was determined that volume/time yield was maximized at a residence time of about 7 hours. The total time from reactor flow start up to establishing the short residence time with maximum yield was between 10 to 12 weeks.

Significant increases in the reduction of the residence time, or even a significant change in the residence time from the initial state to an optimum condition, are generally not achievable because the bio-system would be thrown out of balance.

As already mentioned, the circulating speed is adjusted in accordance with the pH gradient, between the top and bottom parts of the reactor, and is ultimately set in a way that the pH gradient actually disappears. The pH in the reactor increases, in the first place, due to the reduction in the acetic acid concentration caused by decomposition and, in the second place, as a result of the buffering action of the carbonic acid which forms, so that, under stationary conditions, a pH of between about 6.7 to 7.0 is established within the reactor.

EXAMPLE 1

Use was made of the reactor apparatus 1 shown in FIG. 1, in which the reactor vessel 3 had a height of 65 cm and a diameter of 5 cm. It was filled with 300 g of PREUSSAG Filter Anthracite N, ® grain size 1.4 to 2.5 mm. The free reaction volume of the system was 0.76 liters.

The supply was increased in the manner described to 83 ml/h, (residence time: 9.2 h), corresponding to a volume loading of 56 kg-chemical oxygen demand (COD) per m³ per day. A COD reduction of 95% was attained under stationary conditions. In the process, the specific rate of biogas formation was 41 m³ per m³ per day.

EXAMPLE 2

In this test, only 100 g of Filter Anthracite N ® having the same grain size as in Example 1 was loaded into the reactor. The free contact volume was 1.1 liters.

Due to the smaller surface area exposed, substantially less biomass was affixed, so that the operating limit was marked by a residence time of about 17 hours.

Under these conditions, considering the too small amount of support, the volume loading was 32 kg-COD per m³ per day and the specific rate of biogas formation was 19 m³ per m³ per day.

EXAMPLE 3

In a further experiment, 320 g of filter anthracite N of grain size 2.5 to 4.0 mm was loaded into the reactor. In this case, the free contact volume was 0.75 liters. The supply was changed stepwise to 100 ml/h, corresponding to a residence time of 7.5 h and a volume loading of 70 kg COD per m³ per day. With an COD reduction of about 80%, the specific rate of biogas formation was 42 m³ per m³ per day.

EXAMPLE 4

In a further experiment in which use was made of 300 g of Filter Anthracite N, sulfite evaporator condensate (SEC) from the cellulose (pulp and paper) industry and having a chemical oxygen demand of 14 kg per m³ was processed. In addition to acetic acid, the condensate also contained methanol, furfural, formic acid and sulfite. In this case, instead of using the microorganism methanosarcina barkeri which decomposes acetic acid, use was made of a mixed culture which contained microorganisms which additionally decomposed furfural, methanol and oxidized, sulfur compounds.

Within a period of 4 weeks, the residence time could be reduced to 15 hours. The volume loading was 23 kg per m³ per day and the specific rate of biogas formation was 14 m³ per day with a COD reduction of more than 90%.

The process of the invention, which was described in detail on the basis of the decomposition of acetic acid, can be employed, in an analogous manner, for other anaerobic processes which decompose lower carboxylic acids and/or methanol and/or furfural.

What has been described is a process and an apparatus for the continuous decomposition of organic compounds in a fixed-bed reactor.

The invention, as described hereinabove in the context of a preferred embodiment, is not to be taken as limited to all of the provided details thereof, since, modifications and variations thereof may be made without departing from the spirit and scope of the invention.

Recently the mean residence time in the process of anaerobic SEC treatment could be reduced to values between about 4 to 10 hours (dependings upon the special origin of waste water) with COD reduction of ~90%.

Brewery waste water, mainly containing glucose, acetic acid and ethyl alcohol, was purified according to the invention operating with final residence times of 6 to 7 hours.

A surprisingly effective decomposition resulted from the application of porous sintered glass as support for the microorganisms in the fixed-bed reactor.

Particularly, porous borosilicate glass cubes or Raschig rings having a porosity of about 60% to 80% and pore sizes in the order of 50 to 90 μm (receivable from Schott, Mainz, FR Germany) were used as packing material for the fixed bed in the reactor type described above. Employing such a material e.g. in the anaerobic treatment of a high polluted SEC (44 kg-COD per m³), an improvement of volume/time yield by a factor of about two was obtained in comparison to the application of the above mentioned Filter Anthracite N.

What is claimed:

1. A process for the continuous anaerobical decomposition of organic compounds in an aqueous feed solution having a neutralized pH of between about 2 and 4, said solution being subjected, in a reactor, to the action of microorganisms which selectively decompose the compounds in a flow-through process which the production of biogas, said process comprising the steps of:
   (1) introducing said aqueous feed solution into a fixed-bed reactor having microorganisms grown on a fixed-bed material at a first end thereof;
   (2) discharging aqueous flown-through solution from said fixed-bed reactor at a second end thereof;
   (3) recycling a portion of the discharged aqueous solution to the first end of the fixed-bed reactor;
   (4) admixing said recycled portion of discharged aqueous solution with said aqueous feed solution to be introduced into said fixed-bed reactor at the first end thereof;
   (5) measuring the pH at both the first and second ends of said fixed-bed reactor in order to monitor the pH of said reactor bed; and
   (6) selecting said portion of the discharged aqueous flown-through solution to be recycled and admixed with said aqueous feed solution such that the admixture introduced into the fixed-bed reactor maintains the pH of said reactor within a predetermined range of between about 6 and 7.2, such that the pH gradient between the first and second ends of said fixed-bed reactor is within a range of 0.3 pH units maintaining the aqueous solution within the fixed-bed reactor at a temperature of between about 30 and 40° C., and selectively reducing the residence time of the aqueous solution within the fixed-bed reactor until the volume of feed solution introduced into the reactor per unit time is maximized.

2. The process for continuous anaerobic decomposition of organic compounds according to claim 1 wherein a height to diameter ratio of the fixed-bed reactor of a column is between about 8:1 and 16:1.

3. The process for continuous anaerobic decomposition of organic compounds according to claim 2 wherein the column height to diameter ratio is at 12:1.

4. The process for continuous anaerobic decomposition of organic compounds according to claim 1 including the step of introducing a granular support material for the microorganisms with a grain size of between about 2 to 8 mm into the fixed-bed reactor.

5. The process for continuous anaerobic decomposition of organic compounds according to claim 4 wherein the step of said introducing of granular support material for the microorganisms is the introduction of anthracite coal having a grain size of between about 4 to 6 mm.

6. The process for continuous anaerobic decomposition of organic compounds according to claim 4, wherein the step of said introducing of support material for the microorganisms is the introduction of porous sintered glass shapes.

7. The process for continuous anaerobic decomposition of organic compounds according to claim 1 including the steps of: selectively breeding microorganisms in the fixed-bed reactor by autoselection through a means residence time of the aqueous feed solution, which time is not less than 50% of the doubling time of said microorganisms.

8. The process for continuous anaerobic decomposition of organic compounds according to claim 7 wherein the step of reducing the residence time of the aqueous flown-through solution renders a residence time of about 30% of the residence time required to previously establish equilibrium in the reactor bed.

9. In a column reactor for the continuous anaerobic decomposition of organic compounds in an aqueous solution, said reactor having a bottom feed and a top discharge at respective ends thereof, the improvement comprising a fixed-bed reactor for growing microorganisms disposed in said column, means for maintaining the aqueous solution within the fixed-bed reactor at a temperature of between about 30° and 40° C., means for recycling a portion of the discharged aqueous solution to the bottom feed; pH sensors disposed in said column reactor at both said respective ends to provide pH measurements of the aqueous solution within the reactor bed; and means responsive to said pH measurements for selecting the portion of discharged aqueous solution to be recycled, wherein said recycled portion is selected to maintain the pH level within the reactor bed within a predetermined range, whereby the volume of feed solution introduced in the reactor per unit time is maximized upon selective reduction of residence time of the aqueous solution within the reactor.

10. The improved column reactor according to claim 9 wherein the column reactor includes a fluid level regulator means.

11. The improved column reactor according to claim 9 wherein the column has a height to diameter ratio of between about 8:1 and 16:1.

12. The improved column reactor according to claim 11 wherein the column has a height to diameter ratio of 12:1.

13. The improved column reactor according to claim 9 wherein the column reactor has a solid reactor bed comprising granular support material having a grain size of between about 2 to 8 mm.

14. The improved column reactor according to claim 13 wherein the granular material is anthracite coal having a grain size of between about 4 to 6 mm.

15. The improved column reactor according to claim 13, wherein the granular material is formed by porous sintered glass shapes.

16. The improved column reactor according to claim 9 wherein the reactor includes additional measurement means for detecting a pH level within the reactor beyond a predetermined limit; and means for introducing a pH correcting agent into the reactor, said correcting agent introduction means being responsive to said pH measurement means.

* * * * *